United States Patent
Hikosaka et al.

(10) Patent No.: US 11,513,368 B2
(45) Date of Patent: Nov. 29, 2022

(54) LENS UNIT

(71) Applicant: Mitsui Chemicals, Inc., Tokyo (JP)

(72) Inventors: Eiichiro Hikosaka, Nagoya (JP); Ryuki Kan, Nagoya (JP); Akihiro Muramatsu, Marugame (JP); Akifumi Aono, Nagoya (JP)

(73) Assignee: MITSUI CHEMICALS, INC., Tokyo (JP)

( * ) Notice: Subject to any disclaimer, the term of this patent is extended or adjusted under 35 U.S.C. 154(b) by 259 days.

(21) Appl. No.: 16/968,119

(22) PCT Filed: Feb. 7, 2019

(86) PCT No.: PCT/JP2019/004411
§ 371 (c)(1),
(2) Date: Aug. 6, 2020

(87) PCT Pub. No.: WO2019/156164
PCT Pub. Date: Aug. 15, 2019

(65) Prior Publication Data
US 2021/0033890 A1    Feb. 4, 2021

(30) Foreign Application Priority Data
Feb. 9, 2018   (JP) .............................. JP2018-022149

(51) Int. Cl.
*G02C 7/08* (2006.01)
*G02F 1/29* (2006.01)
(Continued)

(52) U.S. Cl.
CPC .............. *G02C 7/083* (2013.01); *G02C 7/06* (2013.01); *G02F 1/29* (2013.01); *G02F 1/294* (2021.01);
(Continued)

(58) Field of Classification Search
CPC ...... G02C 7/02; G02C 7/061; G02C 2202/16; G02C 7/06; G02C 2202/20;
(Continued)

(56) References Cited

U.S. PATENT DOCUMENTS

2005/0030476 A1    2/2005  Dave
2005/0036109 A1    2/2005  Blum
(Continued)

FOREIGN PATENT DOCUMENTS

JP    04-099901 U     1/1991
JP    2004358250 A   12/2004
(Continued)

OTHER PUBLICATIONS

International Search Report from International Application No. PCT/JP2019/004411, dated May 7, 2019.

*Primary Examiner* — Collin X Beatty
*Assistant Examiner* — Grant A Gagnon
(74) *Attorney, Agent, or Firm* — Brundidge & Stanger, P.C.

(57) ABSTRACT

This lens unit comprises: a lens having a liquid crystal lens; a rim part that covers the peripheral edge section of the lens; a control unit that controls the liquid crystal lens; a conductive part that electrically connects the control unit and an electrode end section of the liquid crystal lens which is exposed at the peripheral edge section of the lens, and that is disposed between the rim part and the peripheral edge section of the lens; and a knob part that protrudes from the lens or rim part.

16 Claims, 10 Drawing Sheets

(51) Int. Cl.
*G02C 7/06* (2006.01)
*H02J 50/40* (2016.01)
*H02J 7/02* (2016.01)

(52) U.S. Cl.
CPC ...... *G02F 2201/12* (2013.01); *G02F 2203/01* (2013.01); *H02J 7/02* (2013.01); *H02J 50/40* (2016.02)

(58) Field of Classification Search
CPC ...... G02C 2202/22; G02C 7/04; G02C 7/083; G02C 7/12; G02C 7/028; G02C 7/101; G02C 7/027; G02C 7/044; G02C 7/102; G02C 2202/12; G02C 7/042; G02C 7/022; G02C 7/041; G02C 2202/18; G02C 7/049; G02C 7/085; G02C 7/08; G02C 11/10; G02C 7/104; G02C 7/021; G02C 7/108; G02C 7/10; G02C 7/066; G02C 13/003; G02C 7/048; G02C 7/068; G02C 7/105; G02C 11/08; G02C 2202/14; G02C 2202/10; G02C 7/024; G02C 7/16; G02C 2202/08; G02C 5/00; G02C 5/001; G02C 13/005; G02C 7/063; G02C 7/065; G02C 7/086; G02C 2202/24; G02C 7/047; G02C 7/14; G02C 7/081; G02C 9/00; G02C 7/088; G02C 7/025; G02C 2202/02; G02C 7/043; G02C 11/00; G02C 11/12; G02C 3/003; G02C 7/00; G02C 7/046; G02C 7/107; G02C 2202/06; G02C 1/00; G02C 2200/08; G02C 5/14; G02C 5/146; G02C 7/045; G02C 1/02; G02C 11/02; G02C 2200/02; G02C 5/2263; G02C 1/04; G02C 1/06; G02C 11/06; G02C 2202/04; G02C 7/165; G02C 11/04; G02C 13/001; G02C 3/02; G02C 5/126; G02C 1/10; G02C 2200/12; G02C 2200/22; G02C 5/2254; G02C 9/02; G02C 5/02; G02C 5/16; G02C 5/22; G02C 1/023; G02C 2200/04; G02C 5/005; G02C 5/006; G02C 5/10; G02C 5/20; G02C 9/04; G02C 1/08; G02C 13/00; G02C 3/00; G02C 5/008; G02C 5/04; G02C 5/06; G02C 5/08; G02C 5/122; G02C 5/124; G02C 5/2209; G02C 5/2218; G02C 5/2272; G02F 1/294; G02F 1/29; G02F 1/133526; G02F 1/134309; G02F 1/133371; G02F 1/133553; G02F 1/13415; G02F 1/1345; G02F 1/13452; G02F 1/1341; G02F 1/133377; G02F 1/1334; G02F 2203/28; G02F 1/1333; G02F 2203/18; G02F 1/13; G02F 1/1313; G02F 1/153; G02F 1/161; G02F 1/291; G02F 1/0121; G02F 1/133502; G02F 1/134336; G02F 1/13718; G02F 1/1524; G02F 1/1533; G02F 1/155; G02F 1/0147; G02F 1/132; G02F 1/13318; G02F 1/13324; G02F 1/133345; G02F 1/13338; G02F 1/1335; G02F 1/133528; G02F 1/133634; G02F 1/1339; G02F 1/134318; G02F 1/134363; G02F 1/13439; G02F 1/13471; G02F 1/136; G02F 1/136209; G02F 1/136218; G02F 1/136277; G02F 1/136281; G02F 1/136286; G02F 1/1368; G02F 1/15165; G02F 1/157; G02F 1/163; G02F 1/315; G02F 2001/15145; G02F 2201/083; G02F 2201/42; G02F 2202/14; G02F 2203/12; G02F 2203/50
USPC .................................................... 351/159
See application file for complete search history.

(56) References Cited

U.S. PATENT DOCUMENTS

| | | |
|---|---|---|
| 2010/0177277 A1 | 7/2010 | Kokonaski |
| 2013/0250233 A1 | 9/2013 | Blum |
| 2014/0028966 A1 | 1/2014 | Blum et al. |

FOREIGN PATENT DOCUMENTS

| | | |
|---|---|---|
| JP | 2007-503008 A | 2/2007 |
| JP | 2007-143705 A | 6/2007 |
| JP | 2012-514773 A | 6/2012 |
| JP | 2013-541730 A | 11/2013 |
| JP | 2015016001 A | 1/2015 |
| JP | 2015-522842 A | 8/2015 |
| WO | 2012006631 A2 | 1/2012 |
| WO | 2012/036638 A1 | 3/2012 |

LENS UNIT

TECHNICAL FIELD

The present invention relates to a lens unit.

BACKGROUND ART

Allowing users to experience desired lenses have been conducted by attaching a frame member without a lens to a lens that is independent of the frame member and is detachable to the frame member, and letting the users wear the frame member. Such a frame member is referred to as an optometric frame, a trial frame, a test frame, or a universal frame. Such a lens is referred to as an optometric lens, a trial lens, and/or the like.

PTL 1 discloses an optometric lens using a bifocal, multifocal, or progressive refractive index lens.

In recent years, an eyewear including a lens having an electric element has been used for various use. For example, PTL 2 discloses an eyewear including a liquid crystal lens whose refractive index changes.

When using the lens having the electric element, it is necessary to supply electric power to the electric element. In the eyewear disclosed in PTL 2, a conductive path for electrically connecting between an electric power source provided at the end of a temple and an electrical contact disposed along the upper edge of a lens is provided inside the temple and a frame.

CITATION LIST

Patent Literature

PTL1
Japanese Patent Application Laid-Open No. 2004-358250
PTL 2
Japanese Unexamined Patent Application Publication (Translation of PCT Application) No. 2015-522842

SUMMARY OF INVENTION

Technical Problem

There is a request to let the user experience the change in the viewing way due to the drive of the electric element by attaching the optometric lens having the electric element to the frame member and letting the user wear the frame member. However, since the optometric lens is independent of the frame member, the path for electrically connecting between the electric power source and the electric element cannot be disposed inside the frame or the temple, like the eyewear disclosed in PTL 2, In view of the above circumstances, it is an object of the present invention to provide a lens unit independent of a frame member, the lens unit including an electric element and means for supplying electric power to the electric element.

Solution to Problem

The lens unit according to the present invention includes: a lens unit, comprising: a lens having an electrical element; a rim portion covering a peripheral edge portion of the lens; a control unit for controlling the electrical element; an electric power supply unit for supplying electric power to the electrical element; a conductive portion being disposed between the rim portion and the peripheral edge portion of the lens and electrically connecting between an end portion of an electrode of the electrical element and the control unit, the end portion of the electrode being exposed to the peripheral edge portion; and a knob portion protruding from the lens or the rim portion.

Advantageous Effects of Invention

According to the present invention, there is provided a lens unit independent of a frame member, the lens unit having an electric element and means for supplying electric power to the electric element.

DESCRIPTION OF EMBODIMENTS

Hereinafter, a lens unit according to an embodiment of the present invention will be described. The lens unit according to the present embodiment has a structure independent of a frame member, and can be attached to and detached from the frame member, and is, for example, the lens unit called an optometric lens, a trial lens, and/or the like. The lens unit according to the present embodiment is used by being attached to the frame member called an optometric frame, a test frame, a universal frame, and/or the like for the purpose of adjusting the diopter of the lens to the user or letting the user experience a desired lens, at the time of creation of eyewear such as glasses and/or the like.

[Configuration of Lens Unit 100]

Figure 1A:
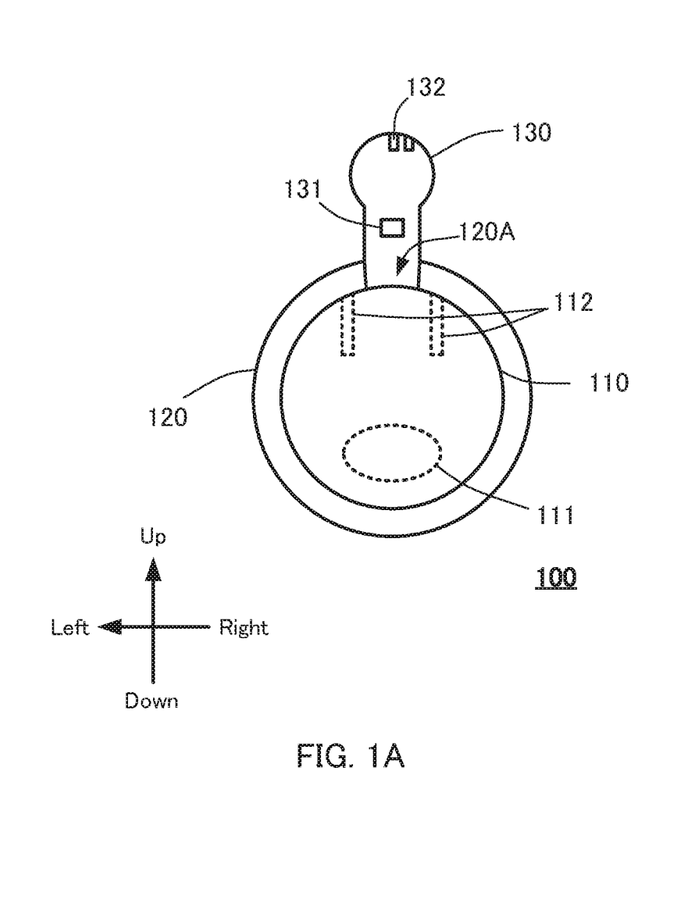
FIG. 1A is a diagram illustrating an external appearance of lens unit according to the present embodiment.
Figure 1B:
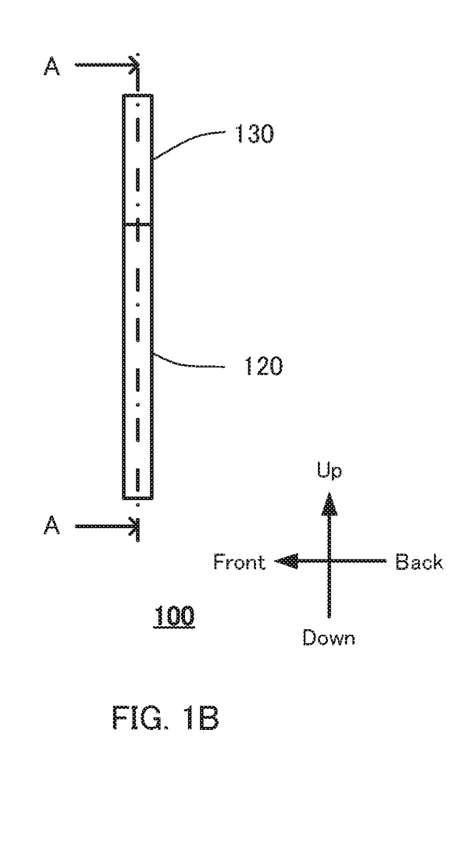
FIG. 1B is a diagram illustrating an external appearance of lens unit according to the present embodiment.

FIG. 1 is a diagram illustrating an external appearance of lens unit 100 according to the present embodiment. FIG. 1A is a front view of lens unit 100, and FIG. 1B is a side view of lens unit 100. The front-back direction, the up-down direction, and the left-right direction of FIG. 1A and FIG. 1B correspond to the direction when viewed from the user with lens unit 100 attached to the frame member, respectively.

As illustrated in FIG. 1A, lens unit 100 has lens 110, rim portion 120, and knob portion 130.

Lens 110 includes liquid crystal lens 111 and a pair of electrodes 112.

Lens 110 has a multilayer structure in which a plurality of layers overlap in the thickness direction, and has a pair of conductive layers sandwiching the liquid crystal layer from the front and rear at a region having liquid crystal lens 111. A pair of conductive layers are connected to electrodes 112, respectively. By applying a voltage between a pair of conductive layers through electrode 112, it is possible to activate the liquid crystal layer and change the refractive index of liquid crystal lens 111. Liquid crystal lens 111 is an example of the electric element and the optical element of the present invention. Details of the electric power supply path to liquid crystal lens 111 via electrode 112 will be described later.

Lens unit 100 is, for example, a bifocal lens, liquid crystal lens 111 is used for short distance, the other regions of lens 110 is used for long distance, respectively. The position of liquid crystal lens 111 is desired to be disposed at a lower position of lens 110 as viewed from the user in a state of being attached to the frame member (see FIG. 1A). The addition (difference between the diopter for long distance power and the short distance) of liquid crystal lens 111 is 0.75D, for example. Note that the present invention is not limited to such a configuration, and may adopt a configuration that a ring electrode is adopted and a plurality of liquid crystal lenses are stacked, so that the addition can be changed. In this case, it may be configured to change the addition of liquid crystal lens 111 in response to the operation to operation portion 131 to be described later.

Lens 110 is formed by cutting out from a lens blank (not illustrated) serving as a base material. As illustrated in FIG. 1A, in the present embodiment, lens 110 has a substantially circular shape. The present invention is not limited to this. The shape of lens 110, in addition to the circular shape, for example, rectangular, trapezoidal, elliptical shape, a shape obtained by combining some of these shapes, or an indefinite shape and/or the like.

Rim portion 120 is a member that covers the periphery of lens 110 and holds lens 110. Examples of the material of rim portion 120 include metals such as titanium, aluminum, and stainless steel, and resins such as polyamide, acetate, celluloid, polyetherimide, and polyurethane, or carbon and/or the like. As described above, it is assumed that lens unit 100 according to the present embodiment is used by being appropriately attached to or detached from the frame member. Therefore, in order to prevent wear and deformation and/or the like due to multiple times of attachment and detachment, at least the portion of rim portion 120 which is exposed to the outside is desirably made of a highly durable material such as metal.

The thickness of lens 110 and rim portion 120 (the length of lens 110 along the optical axis direction) is not particularly limited in the present invention. It is desirably about 3 mm in order to be attachable to and detachable from the frame member such as the optometric frame or the test frame.

Knob portion 130 is a member to be pinched when the user handles lens unit 100. By pinching knob portion 130, the user can easily attach lens unit 100 to the frame member.

The material of knob portion 130 is not particularly limited, may be formed of the same material as that of rim portion 120, or may be formed of a material different from that of rim portion 120. Knob portion 130 may be formed integrally with rim portion 120, or may be formed separately. In the case that knob portion 130 is formed separately from rim portion 120, knob portion 130 may be fixed to a part of the peripheral edge portion of lens 110 or may be fixed to a part of rim portion 120. FIG. 1 illustrates, as an example, a case where opening 120A is provided in a part of rim portion 120, and knob portion 130 is fixed to a part of the peripheral edge portion of lens 110 through opening 120A.

As illustrated in FIG. 1A, operation portion 131 for receiving an operation for changing the refractive index of liquid crystal lens 111 is provided at knob portion 130. In the present embodiment, as an example, operation portion 131 is a detection pad of an electronic capacity type that can be used as a touch sensor, and detects a change in capacitance caused by a contact when an object (e.g., a finger of the user) comes into contact with the detection pad. In the case that knob portion 130 is formed of a material having a metal and/or the like conductivity, for example, a member (not illustrated) having an insulating property around operation portion 131 is disposed, and operation portion 131 and knob portion 130 is insulated.

As another example, for example, operation portion 131 may be a wireless communication device that receives an on/off instruction performed by an on/off operation on a switch provided separately from lens unit 100 by wireless communication. As the wireless communication device of operation portion 131, for example, the communication device corresponding to Wi-Fi (registered trademark), Bluetooth (registered trademark), and/or the like may be used.

Charging terminal 132 in the case of performing charging relative to electric power supply unit 160 (see FIG. 2) described later is provided at knob portion 130.

[Electric Power Supply Path to Liquid Crystal Lens 111]

Figure 2:
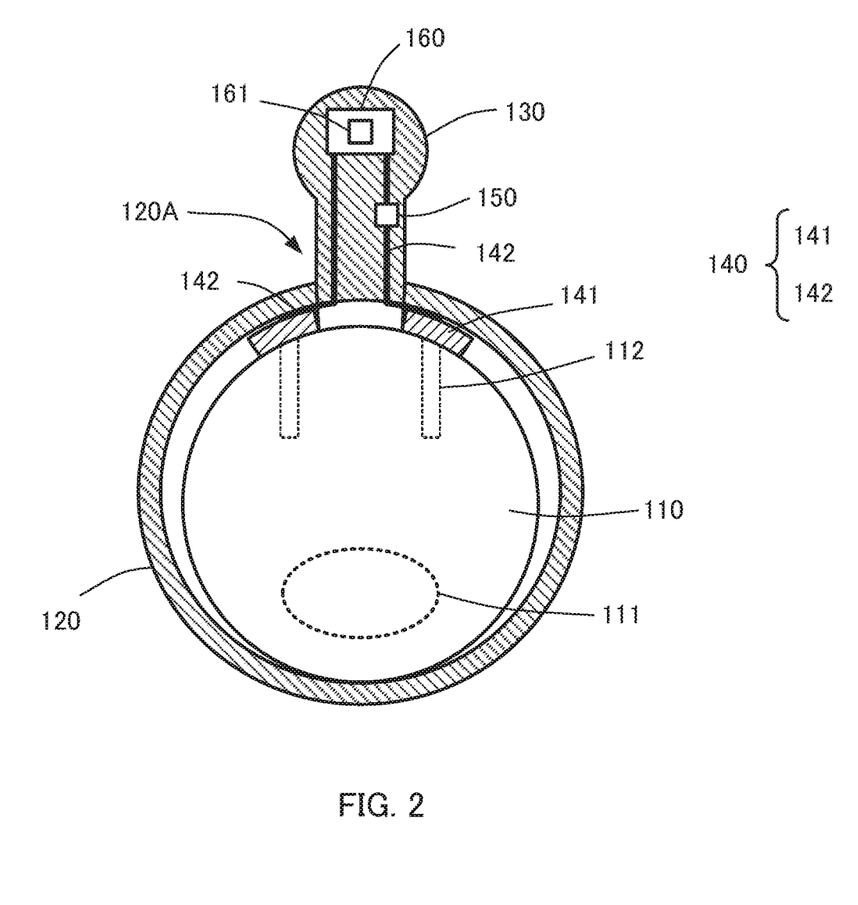
FIG. 2 is a cross-sectional view along line A-A of FIG. 1B.

Next, the electric power supply path to liquid crystal lens 111 of lens 110 will be described in detail. Conductive portion 140 as the electric power supply path has conductive piece 141 and flexible substrate 142, as illustrated in FIG. 2. Conductive portion 140 connects electrode 112 of liquid crystal lens 111 to control unit 150 and electric power supply unit 160. FIG. 2 is a cross-sectional view along line A-A of FIG. 1B.

As illustrated in FIG. 2, a pair of conductive pieces 141 are disposed between lens 110 and rim portion 120. Conductive piece 141 is formed so as to have a constant or more length in a direction along the peripheral edge portion of lens 110. Each of a pair of conductive pieces 141 is electrically connected to a corresponding one of the ends of a pair of electrodes 112 exposed from the peripheral edge portion of lens 110.

For describing that conductive piece 141 is disposed between lens 110 and rim portion 120, FIG. 2 illustrates the distance between lens 110 and rim portion 120 emphasized. However, lens unit 100 of the present embodiment, as actually illustrated in FIG. 1A, has a configuration in which the spacing of lens 110 and rim portion 120 on the exterior appearance is not widened.

Conductive piece 141 is formed of a material having flexibility and conductivity, such as, for example, conductive rubber. Conductive piece 141 is disposed between lens 110 and rim portion 120 in a condition of being compressed by lens 110 and rim portion 120. Thus, as illustrated in FIG. 1A, a configuration in which the spacing of lens 110 and rim portion 120 on the exterior appearance is not widened is realized. Since conductive piece 141 has flexibility, even when disposed in the compressed state, occurring distortion due to being applied excessive stress to lens 110 is prevented.

As illustrated in FIG. 2, a pair of conductive pieces 141 connected to a pair of electrodes 112, respectively, are spaced apart from each other in the direction along the peripheral edge portion of lens 110. Although not particularly limited in the present invention about the distance between a pair of conductive pieces 141 to each other, it is desirable that conductive pieces 141 to each other are disposed apart more than a distance reliably insulated. FIG. 2 illustrates an example in which each of a pair of conductive pieces 141 is disposed so as to avoid opening 120A of rim portion 120. With such a configuration, situations such that a pair of conductive pieces 141 are short-circuited in contact with each other, liquid crystal lens 111 does not operate normally, or liquid crystal lens 111 is destroyed and/or the like can be prevented.

With a configuration that conductive piece 141 is disposed in the compressed state between the peripheral edge portion of lens 110 and rim portion 120, the contact pressure between conductive piece 141 and electrode 112 is sufficiently increased. It is possible to ensure conduction between conductive piece 141 and electrode 112.

The reason that electrode 112 of lens 110 and flexible substrate 142 are electrically connected via conductive piece 141, rather than directly, is as follows. As described above, lens 110 is formed by cutting out from the lens blank. The position of electrode 112 at the peripheral edge portion of lens 110 changes in accordance with the cutting out way from the lens blank. However, changing the design of the electric power supply path to liquid crystal lens 111 of lens 110 in accordance with the position of electrode 112 causes an increase in cost and a prolonged development period and is undesirable. In the present invention, by disposing conductive piece 141 having the constant or more length in the direction along the peripheral edge portion of lens 110, the positional change of electrode 112 in the peripheral edge portion of lens 110 is absorbed.

Each of a pair of conductive pieces 141, flexible substrate (also referred to as flexible printed wiring board or FPC) 142 is electrically connected. Flexible substrate 142 is an example of the conductive wire of the present invention. Flexible substrate 142 has a multilayer structure in which a conductive layer is sandwiched by a pair of insulating layers and the conductive layer is insulated by the insulating layers. At the connection point between flexible substrate 142 and conductive piece 141, and the connection point between flexible substrate 142 and control unit 150, between flexible substrate and electric power supply unit 160, an opening is provided in a part of the insulating layer and conductive layer is exposed. Thus, the electrical connection between conductive piece 141 and the conductive layer of flexible substrate 142 is established. The insulating layer opening that the conductive layer is exposed is formed in such a size that the conductive layer does not contact other than conductive piece 141, control unit 150 or electric power supply unit 160. The conductive layer is insulated from other than conductive piece 141, control unit 150, or electric power supply unit 160. Thus, a short circuit in flexible substrate 142 is prevented.

As illustrated in FIG. 2, flexible substrate 142 is disposed between conductive piece 141 and rim portion 120. Flexible substrate 142 is electrically connected to control unit 150 provided inside knob portion 130 through, for example, the inside of knob portion 130.

The width of flexible substrate 142 in its entirety is less than the width of rim portion 120. In the present specification, the widths of flexible substrate 142 and rim portion 120 mean the length in the direction perpendicular to the sheet of FIG. 1A and FIG. 2, that is, in the thickness direction of lens unit 100. The width of flexible substrate 142 is, for example, 1 mm or more and 3 mm or less. It is desirable that the length along the longitudinal direction of flexible substrate 142 is longer than the linear distance between conductive piece 141 and control unit 150, and is the length so that flexible substrate 142 can be suitably disposed inside knob portion 130. Flexible substrate 142 has a generally elongated shape.

Although FIG. 2 illustrates the structure in which lens 110 includes a pair of electrodes 112, and a pair of conductive pieces 141 and flexible substrates 142 are connected to a pair of electrodes 112 respectively, the present invention is not limited thereto. For example, the number of electrodes 112 may be three or more, in which case, the number of conductive piece 141 and flexible substrate 142 may be the number suited to electrode 112. A single flexible substrate separating a plurality of conductive layers with a plurality of insulating layers may be used to connect between a plurality of electrodes and a plurality of conductive pieces, respectively.

Figure 3:
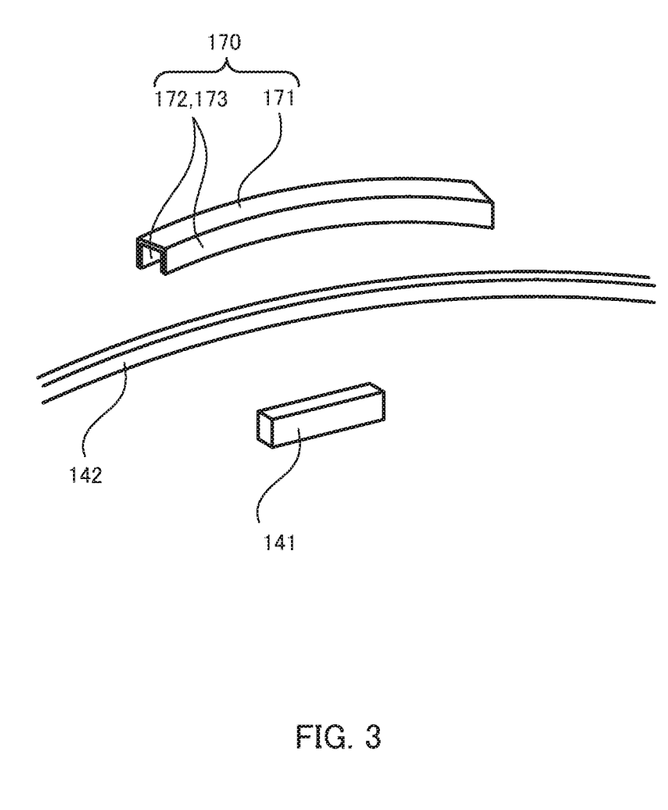
FIG. 3 is a diagram for explaining about an example of use of lens unit according to the present invention.

In the case that rim portion 120 is formed of metal, it is necessary that conductive piece 141 and rim portion 120 are insulated. Lens unit 100 has insulating member 170 (not illustrated in FIG. 2) between rim portion 120 and conductive piece 141, and between rim portion 120 and flexible substrate 142. FIG. 3 is a diagram for explaining insulating member 170. Insulating member 170 is formed of an insulating material such as resin or rubber, for example.

As illustrated in FIG. 3, insulating member 170 has upper plate portion 171 and two side plate portions 172, 173. Upper plate portion 171 is formed so as to be long in a direction along flexible substrate 142. Two side plate portions 172, 173 are connected at substantially right angles toward flexible substrate 142 on both sides of upper plate portion 171. Insulating member 170 is formed so as to be longer than conductive piece 141, in the direction along flexible substrate 142.

In FIG. 3, for the purpose of illustration, insulating member 170, conductive piece 141, and flexible substrate 142 are illustrated in a state of being separated from each other. Actually, insulating member 170, conductive piece 141, and flexible substrate 142 are disposed in a state of being in contact with each other, between rim portion 120 and lens 110 illustrated in FIG. 2. With such a configuration, insulating member 170 is in a state such as to cover conductive piece 141, rim portion 120 and conductive piece 141 are reliably insulated.

Control unit 150 and electric power supply unit 160 are electrically connected to electrode 112 of liquid crystal lens 111, by conductive portion 140 including flexible substrate 142. Although not illustrated, control unit 150 is electrically connected to operation portion 131. Although the method of connecting control unit 150 and operation portion 131 is not particularly limited, control unit 150 and operation portion 131 may be connected by, for example, a cable and/or the like (not illustrated).

Control unit 150 controls, for example, the driving of operation portion 131, the detection of a change in capacitance in operation portion 131, and the application of a voltage to liquid crystal lens 111. Specifically, when operation portion 131 detects the contact of the object (finger and/or the like of the user), the control circuit, for example, applies a voltage to liquid crystal lens 111, or stops the application of the voltage to switch the refractive index of liquid crystal lens 111.

Electric power supply unit 160 supplies electric power to liquid crystal lens 111, operation portion 131, and control unit 150. Electric power supply unit 160 has, for example, rechargeable battery 161 such as a nickel-metal hydride rechargeable battery, and supplies electric power for each configuration using the electric power stored in rechargeable battery 161.

As illustrated in FIG. 2, in the present embodiment, control unit 150 and electric power supply unit 160 are provided inside knob portion 130. The present invention is not limited to this, and for example, a part of control unit 150 and/or electric power supply unit 160 may be disposed between rim portion 120 and lens 110, or a part of control unit 150 and/or electric power supply unit 160 may be exposed to the outside from the outer wall surface of knob portion 130.

[Effect]

As described above, lens unit 100 according to the embodiment of the present invention includes: lens 110 having liquid crystal lens 111; rim portion 120 covering a peripheral edge portion of lens 110; control unit 150 for controlling liquid crystal lens 111; conductive portion 140 being disposed between rim portion 120 and the peripheral edge portion of lens 110 and electrically connecting between the end portion of electrode 112 of liquid crystal lens 111 which is exposed to the peripheral edge portion and control unit 150;

and knob portion 130 protruding from lens 110 or rim portion 120.

Attaching lens unit 100 having such a configuration to a frame member called as, for example, an optometric frame or a test frame let the user experience a change in the refractive index in liquid crystal lens 111. Since lens unit 100 attached to the frame member is freely replaceable, the user can try lens unit 100 having liquid crystal lens 111 of various refractive indices.

According to lens unit 100 according to the embodiment of the present invention, conductive portion 140 includes flexible substrate 142 connected to control unit 150, and conductive piece 141 for electrically connecting between electrode 112 and flexible substrate 142, and a plurality of conductive pieces 141 respectively connected to a plurality of electrodes 112 are disposed apart from each other in a direction along the peripheral edge portion of the lens 110.

With such a configuration, it is possible to reliably insulate a plurality of conductive pieces 141 respectively connected to a plurality of electrodes 112 from each other, and it is possible to prevent malfunction or destruction and/or the like of liquid crystal lens 111 due to a short circuit. By connecting electrode 112 and flexible substrate 142 via conductive piece 141, it is possible to correspond to the positional change of electrode 112 in the peripheral edge portion of lens 110 according to the cutting out way of lens 110 from the lens blank. Since a plurality of conductive pieces 141 are disposed between rim portion 120 and the peripheral edge portion of lens 110, the contact pressure between conductive piece 141 and electrode 112 is sufficiently increased, conduction between conductive piece 141 and electrode 112 becomes reliable.

According to lens unit 100 according to the embodiment of the present invention, rim portion 120 has opening 120A in which knob portion 130 is disposed, and conductive piece 141 is disposed so as to avoid opening 120A.

Since conductive pieces 141 are disposed between the peripheral edge portion of lens 110 and rim portion 120 as described above, even if conductive pieces 141 are disposed while being sufficiently spaced from each other, it is not necessary to increase opening 120A of rim portion 120 more than necessary. Increasing the size of opening 120A more than necessary leads to increasing the size of knob portion 130, which may cause deterioration of the aesthetic appearance and deterioration of the usability of lens unit 100. According to lens unit 100 according to the embodiment of the present invention, it is preferred because such a situation can be prevented.

In lens unit 100 according to the embodiment of the present invention, at least a portion of rim portion 120 which is exposed to the outside is made of metal. With such a configuration, the durability of lens unit 100 is improved, so that lens unit 100 can accommodate multiple times of attachment and detachment to the frame member.

According to lens unit 100 according to the embodiment of the present invention, operation portion 131 that receives an operation on control unit 150 is provided on knob portion 130. With this configuration, a user who attaches lens unit 100 to the frame member for trial use can easily experience changes in the refractive index of liquid crystal lens 111.

Lens unit 100 according to the embodiment of the present invention may be provided with a notification unit (not illustrated) that receives an operation on control unit 150 and notifies the user or the operator (a person other than the user who supports trial use and/or the like of the user) of the change in the refractive index of liquid crystal lens 111 by an LED or sound when the refractive index of liquid crystal lens 111 changes. With such a configuration, the user or the operator who attaches lens unit 100 to the frame member for trial use can recognize that the refractive index of liquid crystal lens 111 has changed based on light or sound other than changes in the refractive index.

[Example of Use]

Hereinafter, an example of use of lens unit 100 of the above embodiment will be described while citing the specific example. First, the frame member to which lens unit 100 of the above embodiment is attached will be described.

<Frame Member>

Figure 4A:
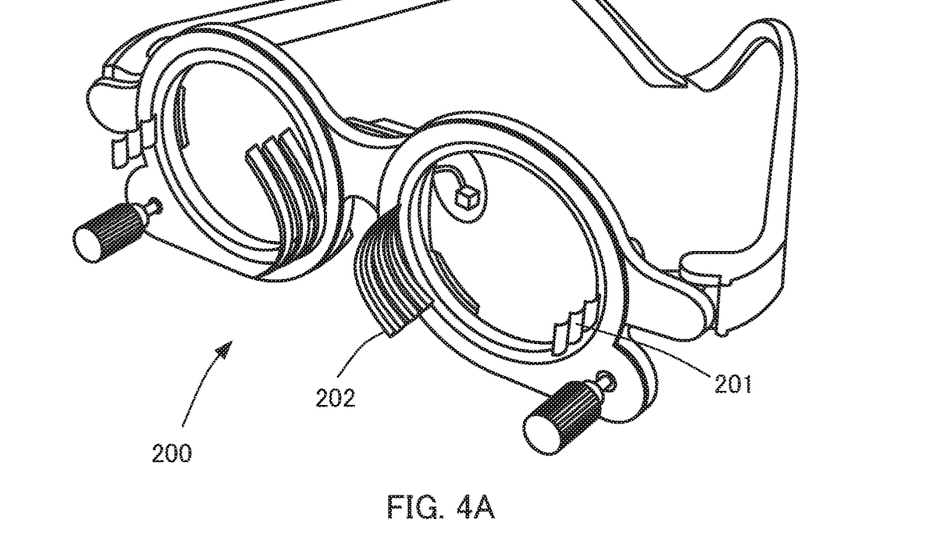
FIG. 4A is a diagrams for illustrating the frame member to which lens unit is attached.
Figure 4B:
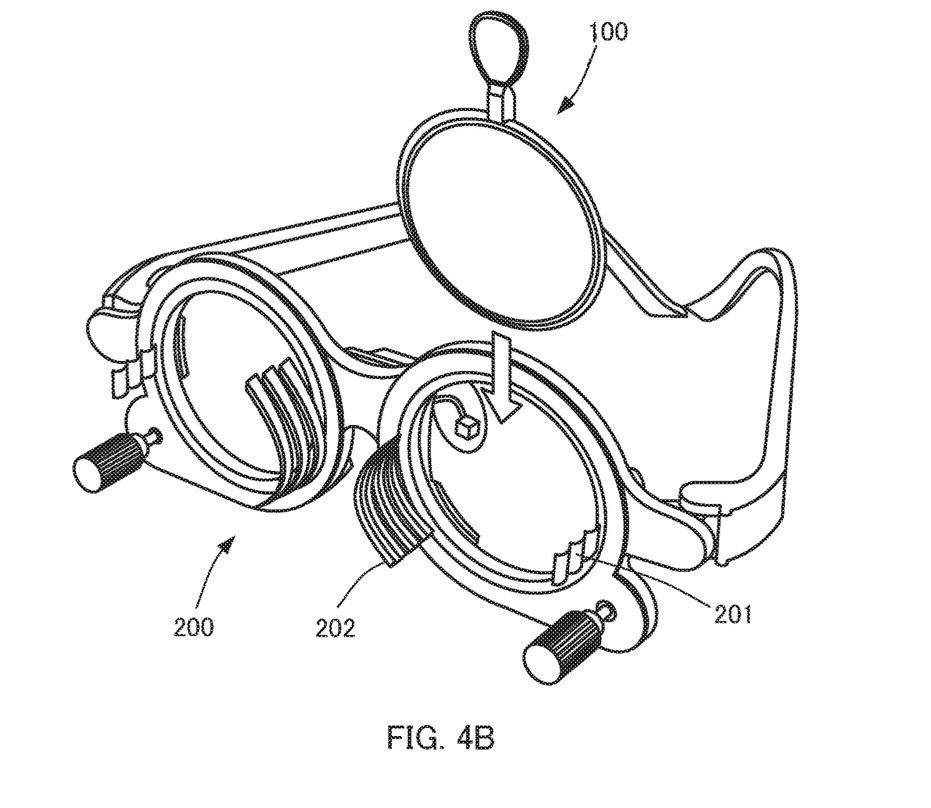
FIG. 4B is a diagrams for illustrating the frame member to which lens unit is attached.

FIG. 4A and FIG. 4B are diagrams for illustrating the frame member to which lens unit 100 is attached. FIG. 4A is a perspective view illustrating an external appearance of frame member 200. As illustrated in FIG. 4A, frame member 200 is configured so as to attach a pair of lens units 100 corresponding to the left and right eyes of the user, respectively. FIG. 4B is a diagram illustrating a state in which lens unit 100 is attached to frame member 200. As illustrated in FIG. 4A, frame member 200 is generally called as the optometric frame, the test frame, the universal frame, and/or the like.

As illustrated in FIG. 4A, frame member 200 has holding members 201 and 202 in the front part. Holding members 201 and 202 hold lens unit 100 when lens unit 100 is attached to frame member 200.

As illustrated in FIG. 4B, lens unit 100 may be attached to frame member 200 by, for example, inserting lens unit 100 between holding members 201 and 202. Although FIG. 4B illustrates an example in which lens unit 100 is attached from the upper side of frame member 200, the present invention is not limited to this. Lens unit 100 may be attached from, for example, the side or the lower side of frame member 200.

<Charging Unit>

Next, a configuration for charging electric power supply unit 160 of lens unit 100 will be described while citing the specific example. In the above embodiment, electric power supply unit 160 performs electric power supply to each configuration of lens unit 100 using the electric power stored in rechargeable battery 161. Therefore, the configuration of charging rechargeable battery 161 before use of lens unit 100 is required.

Figure 5A:
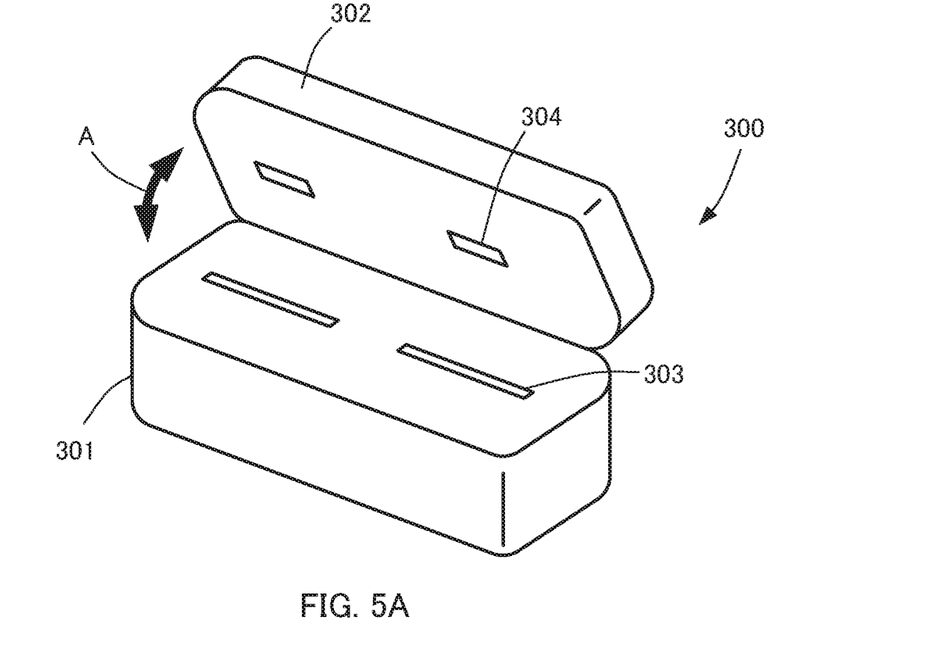
FIG. 5A is a diagram exemplifying charging unit for charging rechargeable battery of lens unit.
Figure 5B:
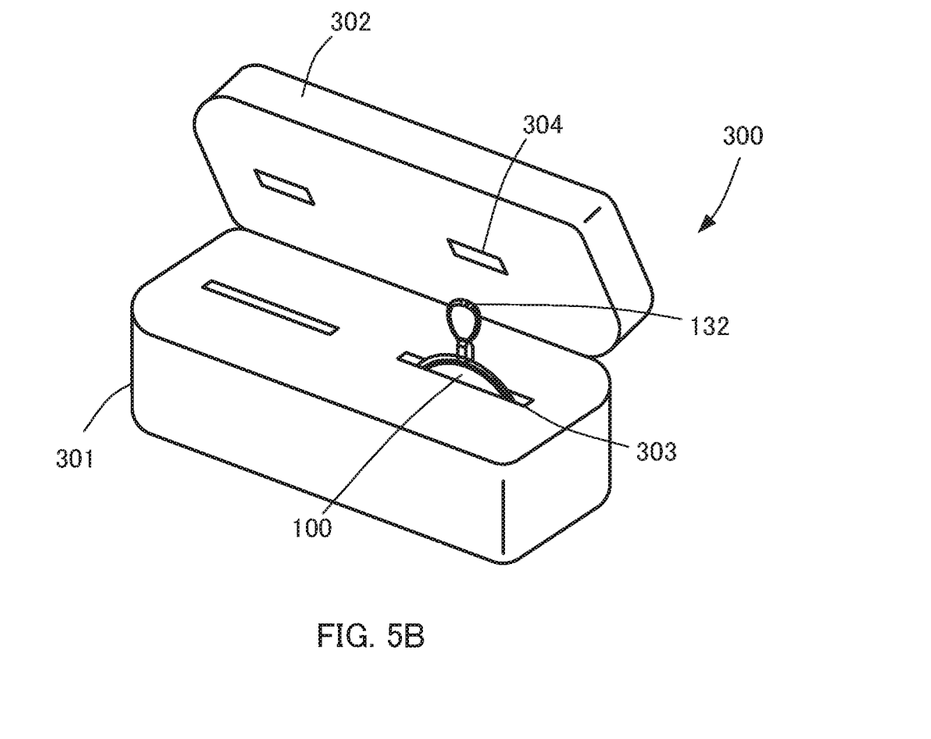
FIG. 5B is a diagram exemplifying charging unit for charging rechargeable battery of lens unit.

FIG. 5A and FIG. 5B are diagrams exemplifying charging unit 300 for charging rechargeable battery 161 of lens unit 100. FIG. 5A is a perspective view illustrating an external appearance of charging unit 300. FIG. 5B is a diagram illustrating a state in which lens unit 100 is charged in charging unit 300.

As illustrated in FIG. 5, charging unit 300 has, for example, base portion 301 and lid portion 302. Lid portion 302 is configured to be opened or closed (arrow A) relative to base portion 301 by a hinge portion (not illustrated). Slit 303 for holding lens unit 100 is provided on base portion 301. Similarly, slit 304 for holding lens unit 100 in a state where lid portion 302 is closed is provided on lid portion 302. It is desirable that at least a portion of base portion 301 and lid portion 302 in contact with lens unit 100 is formed of a soft material (cloth and/or the like) that does not damage lens unit 100.

As illustrated in FIG. 5B, when lens unit 100 is inserted into slit 303 of base portion 301, lens unit 100 is held by base portion 301. When lid portion 302 is closed in this state, knob portion 130 of lens unit 100 is inserted into slit 304 of lid portion 302. An electric power supply terminal (not illustrated) capable of supplying electric power when in contact with charging terminal 132 of knob portion 130 is provided inside slit 304. With such a configuration, when lens unit 100 is put into charging unit 300 and lid portion 302 is closed, charging is performed relative to electric power supply unit 160 (see FIG. 2) via charging terminal 132. When not in use of lens unit 100, it is possible to perform the accommodation and charging of lens unit 100 at the same time in charging unit 300, the usability of lens unit 100 is improved.

Figure 6:
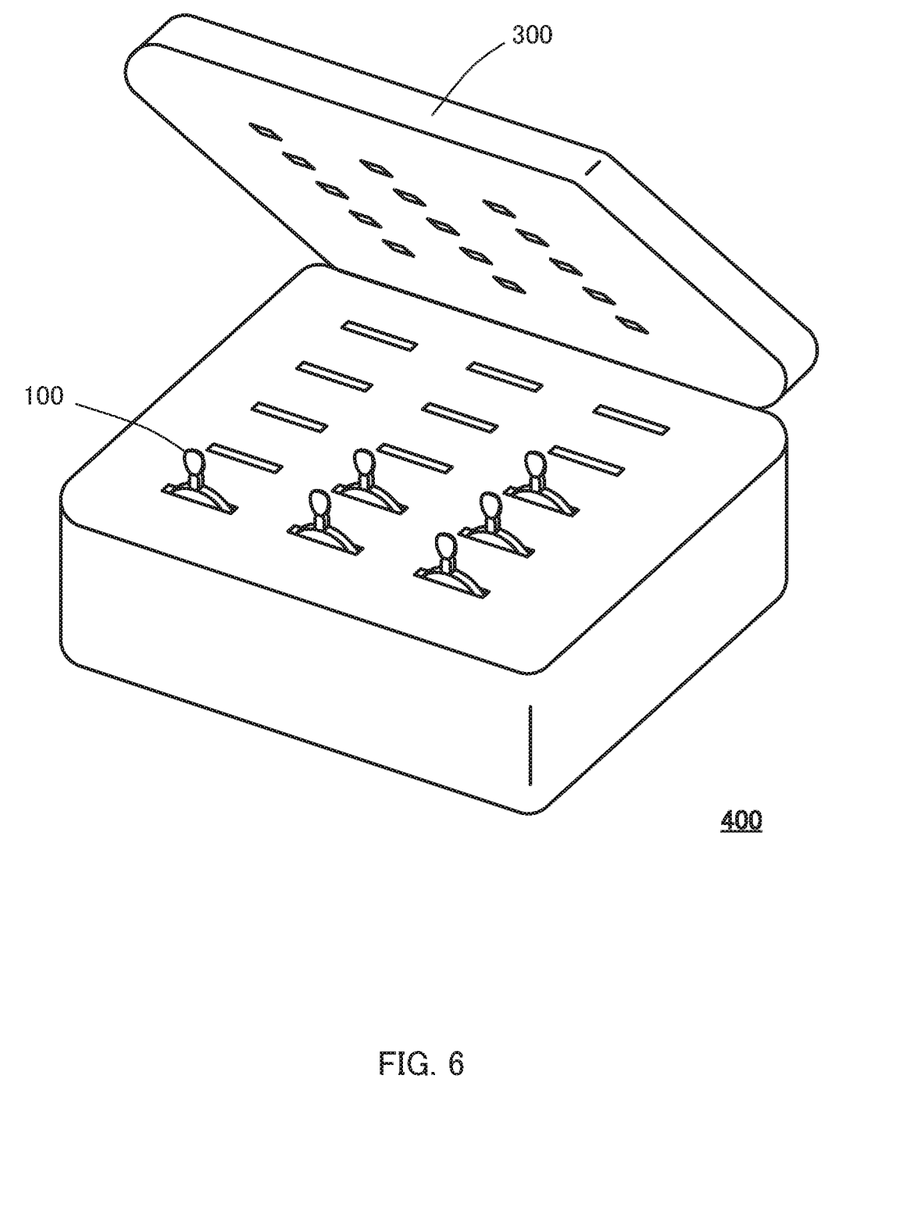
FIG. 6 is a diagram exemplifying a lens set including multiple lens units and charging unit capable of accommodating these.

FIG. 5A and FIG. 5B illustrate an example that charging unit 300 has a pair of slits 303, 304, charging unit 300 may have more slits. In this case, it is more preferable because charging unit 300 can be handled like an accommodation member (case) capable of accommodating and charging a plurality of lens units 100 at the same time. FIG. 6 illustrates an example of lenses set 400 including multiple lens units 100 and charging unit 300 capable of accommodating these.

FIG. 5A and FIG. 5B illustrates an example in which charging unit 300 is held in a state of standing lens unit 100 (a state that knob portion 130 is the upper). Charging unit 300 may hold lens unit 100, for example, in a state in which lens unit 100 is put sideways, i.e., in a state in which knob portion 130 is tilted down in one of the left and right directions. In this case, in charging unit 300, the position of the electric power supply terminal for supplying electric power to charging terminal 132 may be appropriately adjusted.

<Communication Between Multiple Lens Units>

Figure 7:
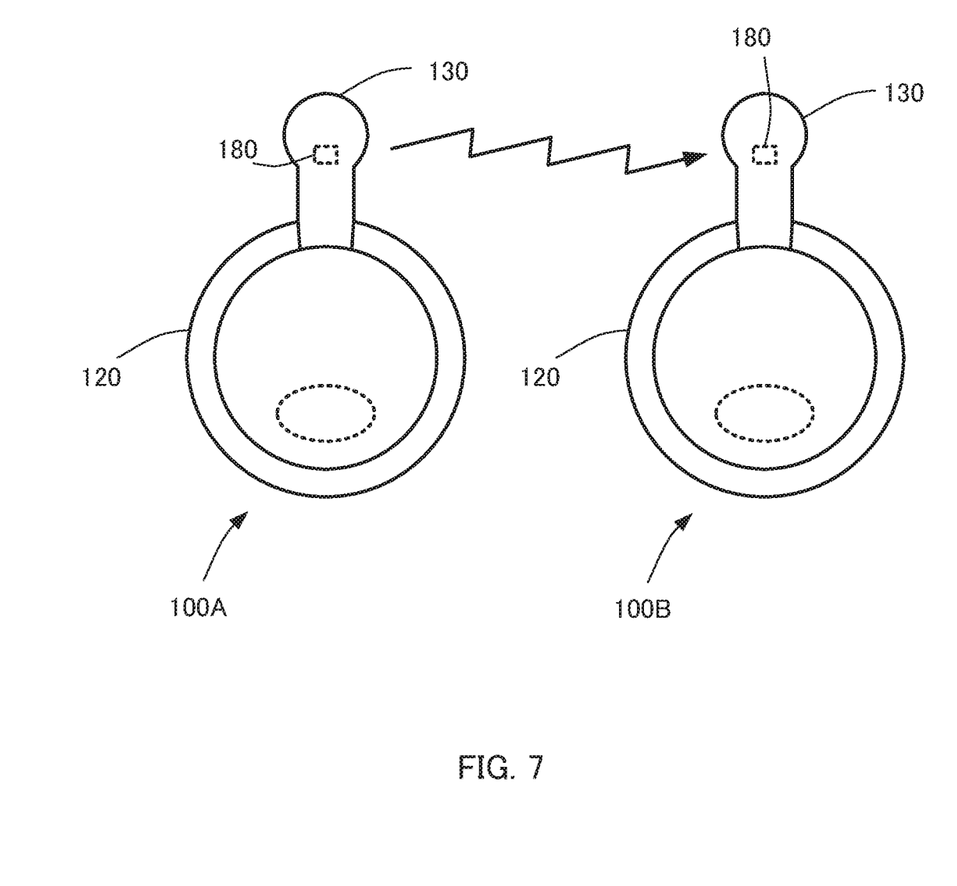
FIG. 7 is a diagram for explaining an example in which wireless communication is performed between a pair of lens units.

In the case that a plurality of lens units is used at the same time, such as the case that a pair of lens units corresponding to the left and right eyes of the user respectively are used at the same time, the lens unit of the present invention may be configured to communicate with each other between the plurality of lens units. FIG. 7 is a diagram for explaining an example in which wireless communication is performed between a pair of lens units 100A and 100B. In the example illustrated in FIG. 7, each of a pair of lens units 100A and 100B has wireless communication unit 180.

When a pair of lens units 100A and 100B are simultaneously used for the left and right eyes of the user, the refractive indices of liquid crystal lenses 111 are preferably adjusted to be substantially the same in the left and right lens units 100A and 100B, because the preferred addition for the user are often substantially the same in the left and right. In such a case, for example, at which time of setting the refractive index of liquid crystal lens 111 suited to the eye of the user by first lens unit 100A, information related to the set refractive index is transmitted to wireless communication unit 180 of second lens unit 100B by using wireless communication unit 180 included in control unit 150. Control unit 150 of second lens unit 100B performs the setting of the refractive index of liquid crystal lens 111 based on the information related to the received refractive index. With such a configuration, in the case that a pair of lens units 100A and 100B are simultaneously used for the left and right eyes of the user, it is possible to omit the labor of adjusting the refractive index for each of the left and right lens units 100A and 100B, thereby improving the usability of lens unit 100.

As wireless communication unit 180, for example, a communication device with a known wireless communication technique, such as Wi-Fi (registered trademark) or Bluetooth (registered trademark) and/or the like may be used. FIG. 7 illustrates an example in which transmission is performed only from first lens unit 100A to second lens unit 100B, it may be configuration so as to communicate in both directions. Wireless communication unit 180 may perform not only communication between a pair of lens units 100A and 100B but also wireless communication with, for example, an external control device (not illustrated). In this case, wireless communication unit 180 receives information related to the designation of the refractive index from the external control device, control unit 150 may control the refractive index of liquid crystal lens 111 based on this information.

[Variations]

In the embodiment described above, as illustrated in FIG. 1A and FIG. 2, in the state that lens unit 100 is attached to the frame member, knob portion 130 is disposed substantially on a straight line passing through the center of liquid crystal lens 111 and the center of lens 110. The present invention is not limited to this. Knob portion 130 may be disposed in an oblique or lateral direction (oriented in a direction perpendicular to the straight line passing through the center of liquid crystal lens 111 and the center of lens 110). With such a configuration, for example, in the case that it is necessary to attach to the frame member with overlapping the other lens and lens unit 100, it can be prevented a situation that the knob portion of the other lens and knob portion 130 of lens unit 100 interfere with each other to be difficult to attach lens unit 100 to the frame member.

In the embodiment described above, as illustrated in FIG. 1B, knob portion 130 is formed so as to extend from lens 110 to the outside in substantially the same plane as lens 110. The present invention is not limited to this. Knob portion 130 may not be disposed in the same plane as lens 110, when viewed from the side of lens unit 100, knob portion 130 may be formed so as to extend obliquely from lens 110. Knob portion 130, for example, may be formed to bend from the middle.

Figure 8A:
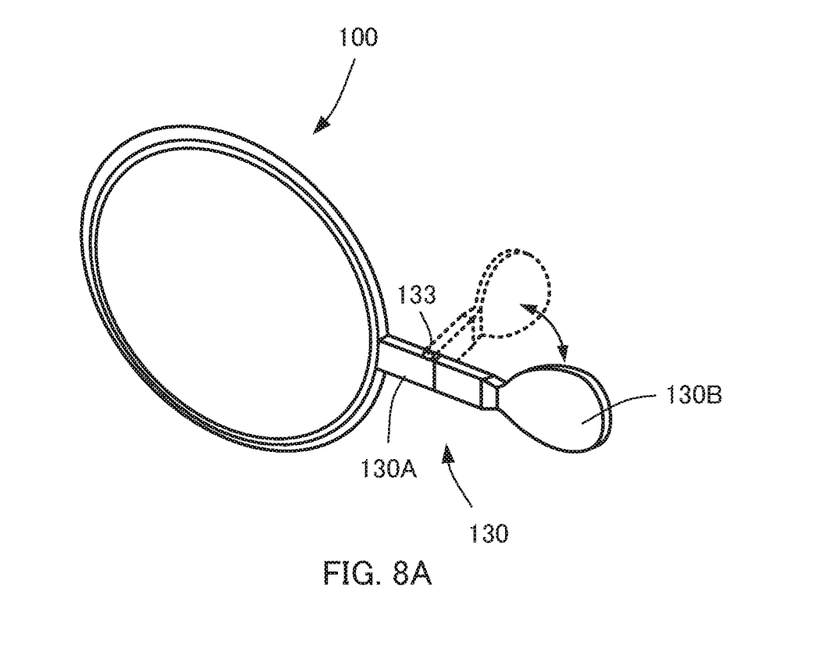
FIG. 8A is a diagram illustrating an example in which knob portion is formed to bend from the middle.

FIG. 8 is a diagram illustrating an example in which knob portion 130 is formed to bend from the middle. As illustrated in FIG. 8A, the portion near the root of knob portion 130 (root portion 130A) is disposed in substantially the same plane as lens 110, and the portion near the tip of knob portion 130 (tip portion 130B) is bent from the same plane as lens 110 to a substantially right angle. The root of tip portion 130B is provided with hinge portion 133. It is configured that the user can bend tip portion 130B against root portion 130A or return to its original state (extended state) by using hinge portion 133 as a fulcrum.

Figure 8B:
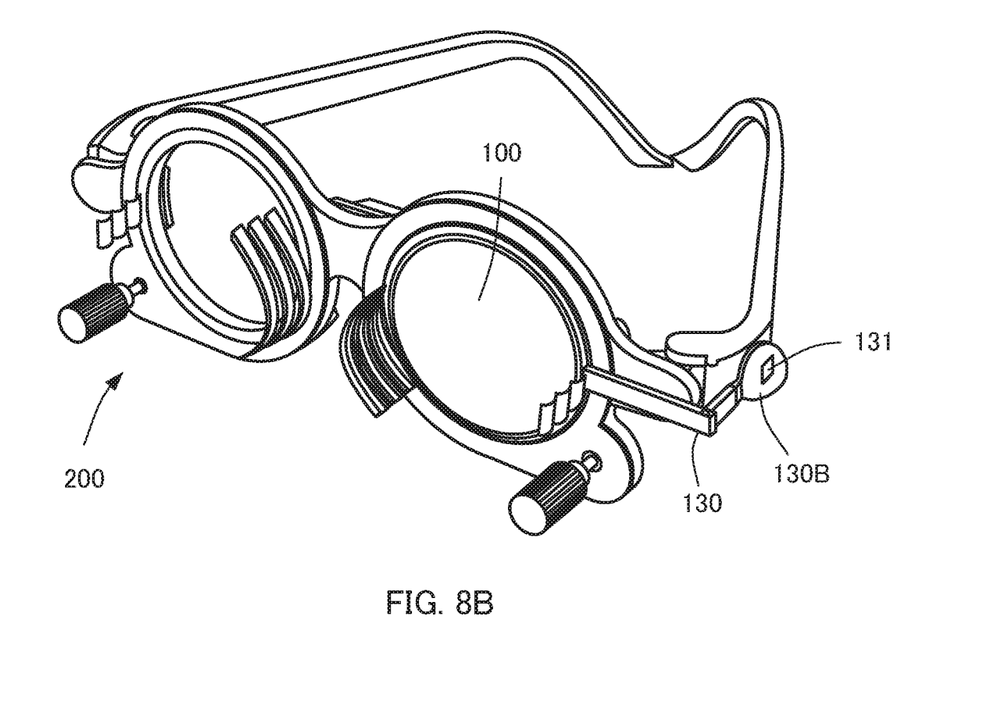
FIG. 8B is a diagram illustrating an example in which knob portion is formed to bend from the middle

In such a case, it is desirable that operation portion 131 is provided in tip portion 130B. The reason is that in a condition of attaching lens unit 100 to frame member 200, operation portion 131 is positioned at a position that the user is easy to operate. FIG. 8B is a diagram illustrating an example of use in the case that operation portion 131 is provided in tip portion 130B. FIG. 8B illustrates a situation that lens unit 100 that knob portion 130 having tip portion 130B is disposed sideways is attached to frame member 200 exemplified in FIG. 4.

As illustrated in FIG. 8B, in a state that lens unit 100 is attached to frame member 200, operation portion 131 provided on tip portion 130B is positioned at a position corresponding to a temple of common glasses. Since the temple is a position where a person wearing glasses can easily touch with a hand, the user who uses frame member 200 to which lens unit 100 is attached can preferably operate operation portion 131. In an eyewear such as an electronic glasses having a lens with an electric element, since the operating portion of the electric element is often provided in the temple generally, the user can perform an experience almost the same as the actual operation feeling at the trial use of lens unit 100.

As described in the above example of use, lens unit 100 according to the above embodiment is assumed to be attached to the frame member called the optometric frame, the test frame, and/or the like. The present invention is not limited to this. The lens unit of the present invention may be used not only by being attached to the frame member, but also by being attached to another device such as an optometric device called a phoropter and/or the like.

Figure 9A:
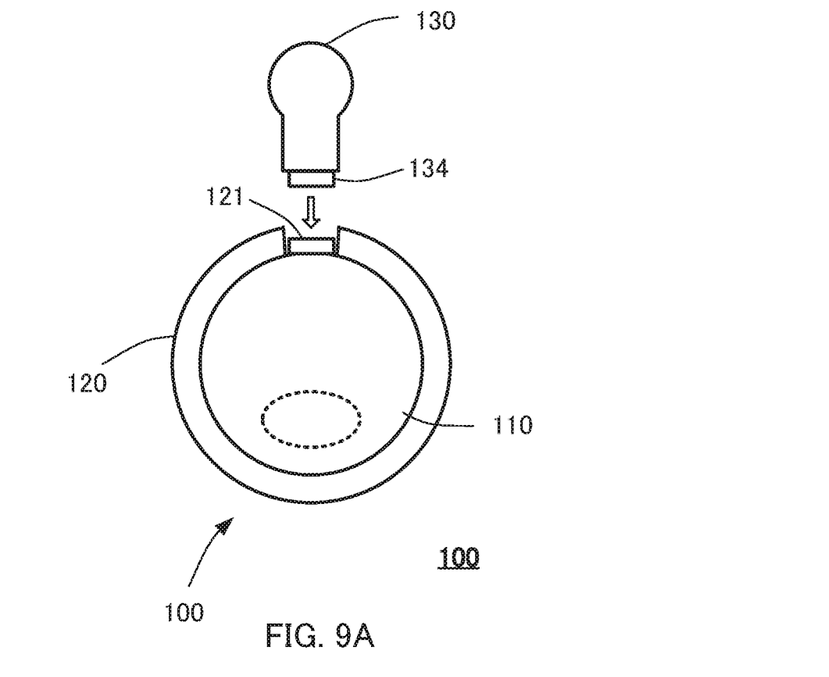
FIG. 9A is a diagram illustrating other example of method of fixing knob portion.
Figure 9B:
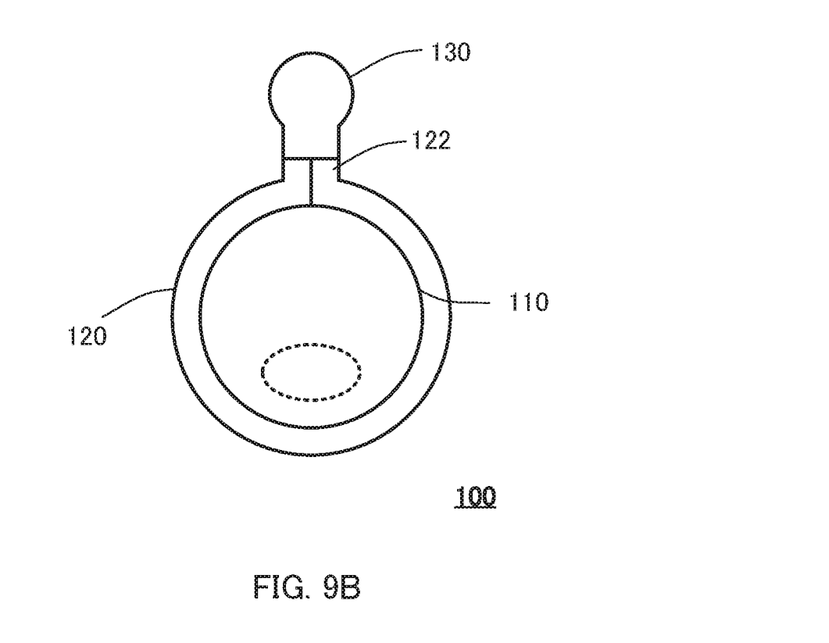
FIG. 9B is a diagram illustrating other example of method of fixing knob portion.

In the embodiment described above, FIG. 1A illustrates case that opening 120A is provided in a part of rim portion 120, and knob portion 130 is fixed to a part of the peripheral edge portion of lens 110 through this opening 120A. The present invention is not limited to this. FIG. 9A and FIG. 9B are diagrams illustrating other examples of methods of fixing knob portion 130.

FIG. 9A is a diagram illustrating an example in which substantially the entirety of knob portion 130 is configured to be detachable relative to the body portion of lens unit 100 (here, the portion including lens 110 and rim portion 120). In the embodiment illustrated in FIG. 9A, connector 121 is provided in rim portion 120, connector 134 is provided in knob portion 130, respectively. Each of connectors 121, 134 has an electrical contact (not illustrated) such as a tab terminal or a USB terminal. When knob portion 130 is attached to rim portion 120, by this electrical contact, electric power supply unit 160 provided inside knob portion 130 and electrode 112 of liquid crystal lens 111 are electrically connected. In the embodiment illustrated in FIG. 9A, it is preferable that electric power supply unit 160 is provided inside knob portion 130 to be removed. Control unit 150 may be provided inside the body portion of lens unit 100, not inside knob portion 130. In this case, control unit 150 will remain in the body portion of lens unit 100 even if knob portion 130 is removed.

With such a configuration, for example, charging can be performed by detaching knob portion 130 and connecting only knob portion 130 to the charger of electric power supply unit 160. Therefore, for example, in the case that the remaining charge amount of electric power supply unit 160 is reduced, it is possible to continuously use lens unit 100 by removing first knob portion 130, and attaching the second knob portion 130 including electric power supply unit 160 whose charge amount is remained sufficiently.

FIG. 9B is a diagram illustrating an example in which rim portion 120 and knob portion 130 are integrally formed. In this example, knob portion 130 is fixed to rim lock 122 which is a member for closing rim portion 120. As a result, knob portion 130 can be firmly fixed.

Figure 10:
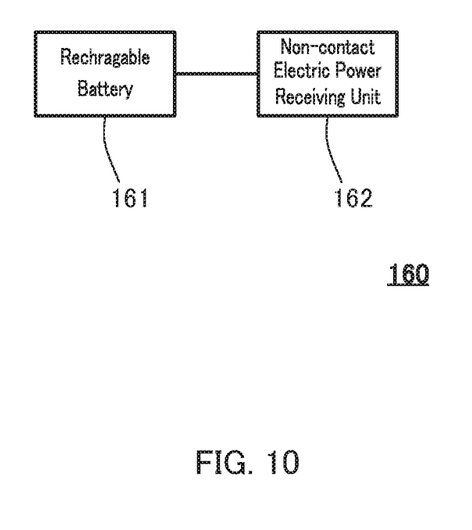
FIG. 10 is a diagram illustrating an example in which electric power supply unit has a non-contact electric power receiving unit.

In the embodiment described above, charging terminal 132 for charging rechargeable battery 161 is provided on non-detachable knob portion 130. The present invention is not limited to this. In the present invention, the charging for rechargeable battery 161 may be performed via, for example, non-contact electric power receiving unit 162 for receiving a non-contact electric power supply from the outside. FIG. 10 is a diagram illustrating an example in which electric power supply unit 160 has a non-contact electric power receiving unit 162.

In the case that non-contact electric power receiving unit 162 receives electric power from the outside, the received electric power may not be used to charge electric power supply unit 160 that is a rechargeable battery, and may be supplied to electrode 112 and control unit 150 directly. In this case, since it is not necessary that electric power supply unit 160 have rechargeable battery 161, it is possible to save space and reduce cost. Since it is not necessary that rechargeable battery 161 is charged before use of lens unit 100, the usability of lens unit 100 is improved.

In the embodiment described above, lens 110 has liquid crystal lens 111 whose refractive index changes by electrical control as an example of the electrical element and the optical element of the present invention. The present invention is not limited to this. As the electric element and the optical element of the present invention, for example, an electrochromic lens in which the transmittance of light is changed by electrical control may be employed. As the electric element and the optical element of the present invention, such as a liquid crystal lens and an electrochromic lens, a composite lens obtained by overlapping a plurality of lenses of different types from each other may be employed. In this case, it is desirable that operation portion 131 corresponding to each lens is provided independently according to the type of the lens.

In the embodiment described above, liquid crystal lens 111 as an example of the optical element has its refractive index changed by the control of control unit 150. The present invention is not limited to this. The lens unit of the present invention has, for example, an optical element whose optical characteristics (refractive index and transmittance of light, and/or the like) is not changed by electrical control, and whose optical characteristics is fixed in a state different from the other regions of the lens. Specifically, for example, by disposing a material (for example, transparent adhesive and/or the like) with different optical characteristics from the other regions of the lens, the lens unit of the present invention may have a region with different optical characteristics regardless of electrical control.

In the embodiment described above, it has been described about the case where knob portion 130, operation portion 131 which is a configuration provided in knob portion 130, control unit 150, and electric power supply portion 160 are provided one by one, respectively. The present invention is not limited to this. The lens unit of the present invention may have a plurality of knobs, operation portions, control units, and electric power supply units. These may be appropriately changed according to the purpose of use, the usage mode, and/or the like of the lens unit.

This application is entitled to and claims the benefit of Japanese Patent Application No. 2018-022149 filed on Feb. 9, 2018, the disclosure of which including the specification, drawings and abstract is incorporated herein by reference in its entirety.

INDUSTRIAL APPLICABILITY

The present invention is preferable as a lens unit including a lens having an electric element.

REFERENCE SIGNS LIST 100,100A, 100B lens unit
110 Lens
111 Liquid crystal lens
112 Electrode
120 Rim portion
120A Opening
121 Connector
122 Rim lock
130 Knob portion
130A Root portion
130B Tip portion
131 Operation portion
132 Charging terminal
133 Hinge portion
134 Connector
140 Conductive portion
141 Conductive piece
142 Flexible substrate
150 Control unit
160 Electric power supply unit
161 Rechargeable battery
162 Non-contact power receiving unit
170 Insulating member
171 Upper plate portion
172,173 Side plate portion
180 Wireless communication unit
200 Frame member
201,202 Holding member
300 Charging unit
301 Base portion
302 Lid portion
303,304 Slit
400 Lens set

What is claimed is:

1. An optometric lens unit, comprising:
   a lens comprising an electrical element;
   a rim portion covering a peripheral edge portion of the lens;
   a control unit for controlling the electrical element;
   an electric power supply unit for supplying electric power to the electrical element;
   a conductive portion being disposed between the rim portion and the peripheral edge portion of the lens and electrically connecting between an end portion of an electrode of the electrical element and the control unit, the end portion of the electrode being exposed to the peripheral edge portion; and
   a knob portion protruding from the lens or the rim portion, and provided with the control unit,
   wherein the optometric lens unit is configured to be attached to and detached from a frame member, and is attached to the frame member when the optometric lens unit is used.

2. The optometric lens unit according to claim 1, wherein the conductive portion includes a conductive wire connected to the control unit, and a conductive piece for electrically connecting between the electrode end portion and the conductive wire.

3. The optometric lens unit according to claim 2, wherein a plurality of the conductive pieces electrically connect between a plurality of electrode end portions and the conductive wires, respectively, and are disposed apart from each other in a direction along the peripheral edge portion of the lens.

4. The optometric lens unit according to claim 3, wherein the plurality of conductive pieces are insulated from each other.

5. The optometric lens unit according to claim 2, wherein:
   the rim portion comprises an opening in which the knob portion is disposed, and
   the conductive piece is disposed to avoid the opening.

6. The optometric lens unit according to claim 2, wherein an insulating member for insulating the conductive piece from the rim portion is disposed between the rim portion and the conductive portion.

7. The optometric lens unit according to claim 1, wherein a portion of the rim portion which is exposed to an outside is made of metal.

8. The optometric lens unit according to claim 1, further comprising an operation portion provided on the knob portion and receiving an operation on the control unit.

9. The optometric lens unit according to claim 1, wherein the knob portion has a hinge portion for rotating a tip portion of the knob portion relative to a root portion of the knob portion.

10. The optometric lens unit according to of claim 1, wherein the electrical element is an optical element whose optical characteristics are changed by electrical control.

11. The optometric lens unit according to claim 10, further comprising a wireless communication unit for performing wireless communication, wherein the wireless communication unit transmits and/or receives information related to control of the optical element.

12. The optometric lens unit according to claim 1, wherein the electric power supply unit includes a rechargeable battery.

13. The optometric lens unit according to claim 12, wherein the knob portion includes a charging terminal for charging the rechargeable battery.

14. The optometric lens unit according to claim 1, wherein the electric power supply portion includes a non-contact electric power receiving section for receiving a non-contact electric power supply from an outside.

15. An optometric lens set, comprising:
   at least one lens unit according to claim 1; and
   a charging unit capable of charging with the lens unit accommodated therein.

16. The optometric lens unit according to claim 1, wherein the knob portion is a portion that is gripped when the optometric lens unit is attached to the frame member.

* * * * *